(12) United States Patent
Lee

(10) Patent No.: US 12,331,925 B2
(45) Date of Patent: Jun. 17, 2025

(54) IPL LIGHT GUIDING DEVICE THAT REALIZES FRACTIONAL BY UTILIZING POLARIZATION FUNCTION

(71) Applicant: A.M.I Inc., Seoul (KR)

(72) Inventor: Hae Yeon Lee, Seoul (KR)

(73) Assignee: A.M.I Inc., Seoul (KR)

( * ) Notice: Subject to any disclaimer, the term of this patent is extended or adjusted under 35 U.S.C. 154(b) by 0 days.

(21) Appl. No.: 18/828,568

(22) Filed: Sep. 9, 2024

(65) Prior Publication Data

US 2025/0093014 A1 Mar. 20, 2025

(30) Foreign Application Priority Data

Sep. 14, 2023 (KR) .................. 10-2023-0122314

(51) Int. Cl.
*F21V 5/04* (2006.01)
*F21V 7/00* (2006.01)
*F21V 17/00* (2006.01)

(52) U.S. Cl.
CPC .............. *F21V 5/04* (2013.01); *F21V 7/0033* (2013.01); *F21V 17/002* (2013.01)

(58) Field of Classification Search
CPC ... F21V 5/04–048; F21V 7/0025–0041; F21V 17/002; F21V 21/40–406
See application file for complete search history.

(56) References Cited

U.S. PATENT DOCUMENTS

2021/0361938 A1 11/2021 Gershonowitz
2024/0149073 A1* 5/2024 Jones ................... A61N 5/0616

FOREIGN PATENT DOCUMENTS

KR 10-2022-0107495 A 8/2022

* cited by examiner

*Primary Examiner* — Jason M Han
(74) *Attorney, Agent, or Firm* — Studebaker Brackett PLLC

(57) ABSTRACT

The present disclosure relates to an IPL light guiding device. The IPL light guiding device include handle for manual operation, a light source equipped inside a reflective casing, and an installment section formed below the light source, lens that is detachably coupled to the installment section, the lens forming three-dimensional body allowing light emitted from the light source to pass through and irradiate the bottom surface, bottom surface of the body including concentrating unit irradiated with light, and reflecting unit formed between the concentrating unit, which reflect light toward the concentrating unit, light emitted from the light source concentrated and irradiated onto the concentrating unit.

7 Claims, 7 Drawing Sheets

IPL LIGHT GUIDING DEVICE THAT REALIZES FRACTIONAL BY UTILIZING POLARIZATION FUNCTION

CROSS-REFERENCE TO RELATED APPLICATION

The present application claims priority to Korean patent application number 10-2023-0122314, filed on Sep. 14, 2023, which is incorporated herein by reference in its entirety.

BACKGROUND

1. Field of Invention

This application relates to an Intense Pulse Light (IPL) light guiding device that realizes fractional by utilizing polarization function. More specifically, the IPL light guiding device optimizes the emission of light from a light source by distinguishing areas where light is concentrated and areas where it is not. This device maximizes the fractional effects, thereby enabling the achievement of optimal treatment outcomes.

2. Description of Related Art

Light irradiators, such as an Intense Pulse Light (IPL) devices used for skin treatments, emit light in the form of strong pulses within a specific wavelength range. These devices are used in clinical procedures for skin beautification, treatment of vascular lesions, and hair removal, among others. The wavelength range, pulse width, interval between pulses, and energy levels are carefully calibrated and harmonized for optimal use.

On the other hand, light irradiators that use laser beams as light source induce fractional effects to treat damaged areas. The term "fractional" refers to the technique of dividing a laser beam into micro-beams, which is used in procedures such as scar and pore treatment. When the laser beam is irradiated, thermal stimulation from the light penetrates the dermis layer, stimulating stem cells and regenerating collagen and elastin to achieve the treatment effect. As a result, fractional effect involves inducing controlled micro-damage to the skin to promote regeneration and heal damaged areas.

Lenses are used in light irradiators to direct the emitted light onto the treatment area to induce the fractional effect. These lenses must be designed to maximize the desired effect by ensuring that the emitted light is optimally focused on the treatment area, necessitating a structure that can achieve the best possible results.

SUMMARY

Various embodiments of the present disclosure are directed to IPL light guiding device with light emitted from the light source concentrated and directed precisely, which induces fractional effects and maximizes the treatment effectiveness, enhancing the overall therapeutic outcomes when practiced on human body.

An embodiment of the present disclosure may provide for an IPL light guiding device. The IPL light guiding device include handle for manual operation, a light source equipped inside a reflective casing, and an installment section formed below the light source, lens that is detachably coupled to the installment section, the lens forming three-dimensional body allowing light emitted from the light source to pass through and be irradiate the bottom surface, bottom surface of the body including concentrating unit irradiated with light, and reflecting unit formed between the concentrating unit, which reflect light toward the concentrating unit, light emitted from the light source concentrated and irradiated onto the concentrating unit.

DETAILED DESCRIPTION

In the disclosure, anatomic laser irradiation lens is proposed in which light emitted from a light source is focused and irradiated on the concentrating unit. Light emitted from the light source was kept at optimal condition and in particular, areas where light is concentrated and areas where it is not was distinguished in order to maximize fractional effects and achieving the best possible treatment outcomes. This lens has a three-dimensional body, allowing light emitted from the light source to pass through and irradiate on the bottom surface. The bottom surface of the body features alternating concentrating unit and reflecting unit, where the reflecting unit are designed to reflect light toward the concentrating unit, ensuring that the light emitted from the light source is focused and irradiated on the concentrating unit.

The following detailed explanation of the disclosure is provided with reference to the attached drawings, FIGS. 1 through 9.

Figure 1:
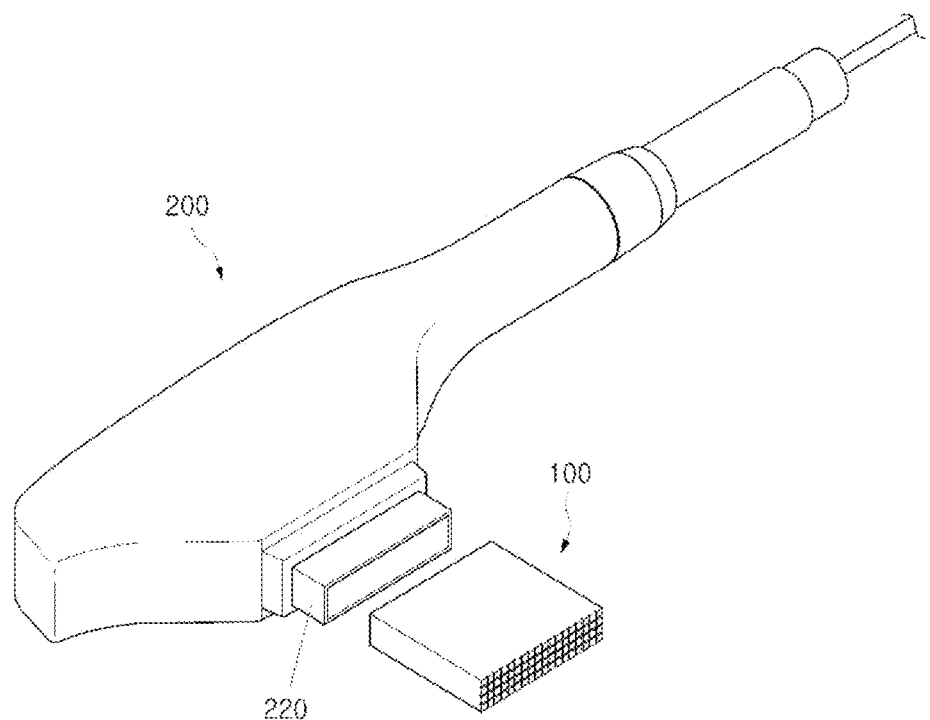
FIG. 1 is an illustrative view of light irradiator according to the disclosure.
Figure 2:
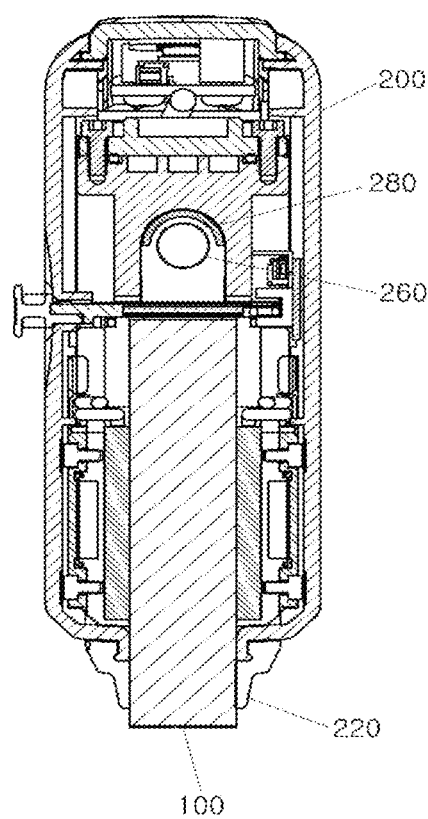
FIG. 2 is an illustrative view showing the arrangement of light source and lens in light irradiator according to the disclosure.

FIG. 1 illustrates an example of the light irradiator according to the disclosure, and FIG. 2 shows the arrangement of the light source and the lens in the light irradiator according to the disclosure.

The lens (100) is equipped on the light irradiator (200) used for skin beautification according to the disclosure.

The light irradiator (200) may include a handle formed on one side for manual operation. Inside, the light source (260) is equipped within a reflective casing (280), and the installment section (220) is formed below the light source (260).

The light source (260) may be a xenon gas lamp of a certain length, and the reflective casing (280) may be hemispherical in cross-section to reflect light only in the direction of the installment section (220), which is also toward the direction of the lens (100).

In this light irradiator (200), the lens (100) according to the disclosure is detachably equipped to the installment section (220).

Figure 3:
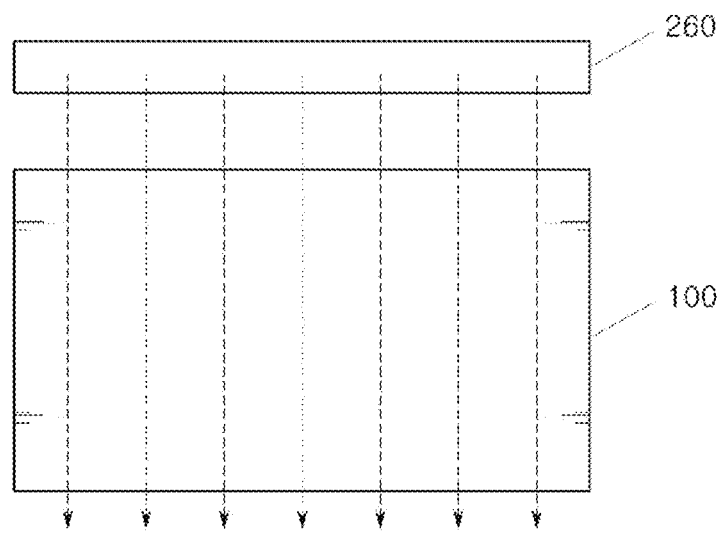
FIG. 3 is an illustrative view showing the relationship between lens and light source according to the disclosure.
Figure 4:
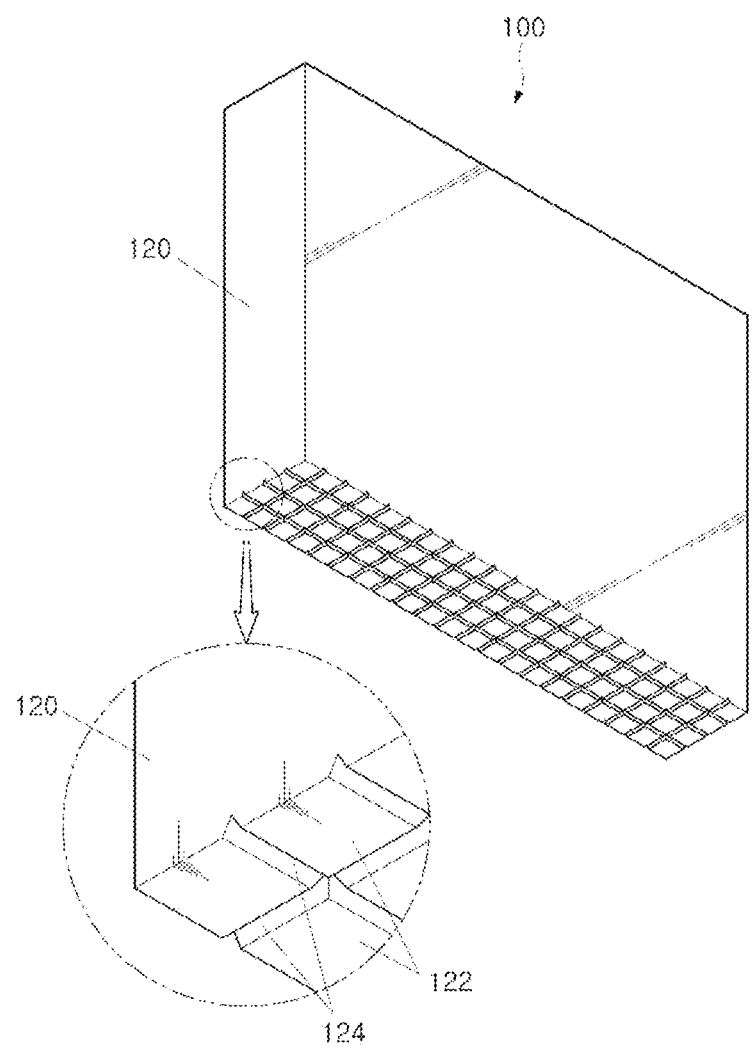
FIG. 4 is an illustrative view of lens according to the disclosure.
Figure 5:
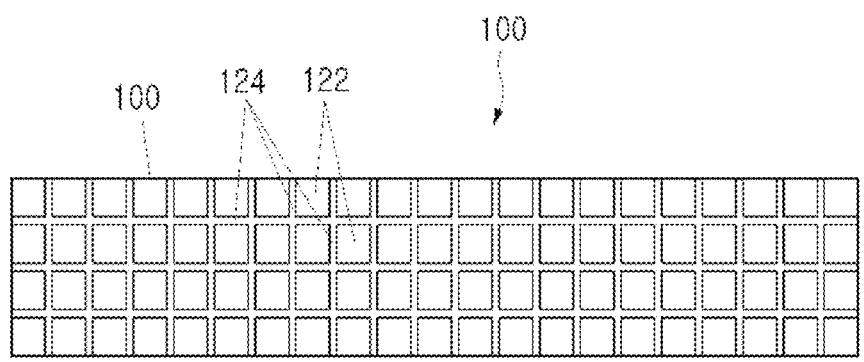
FIG. 5 is a bottom view of lens according to the disclosure.
Figure 6:
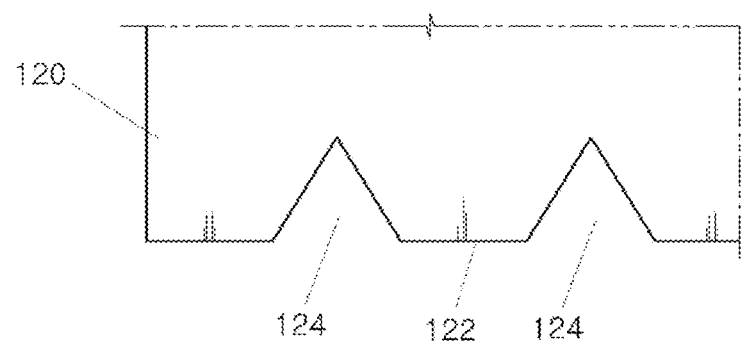
FIG. 6 to FIG. 8 are illustrative views showing the shape of reflecting unit according to the disclosure.
Figure 7:
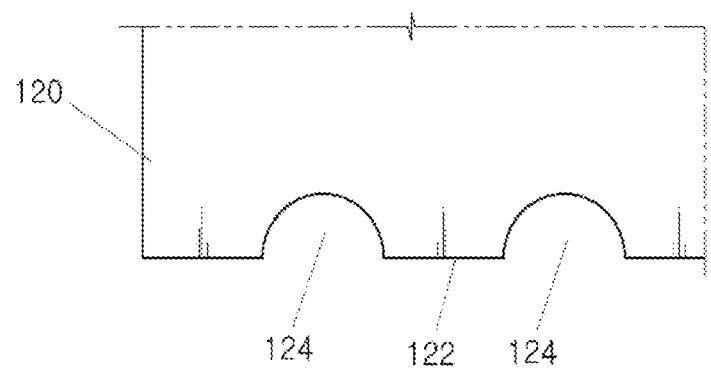
Figure 8:
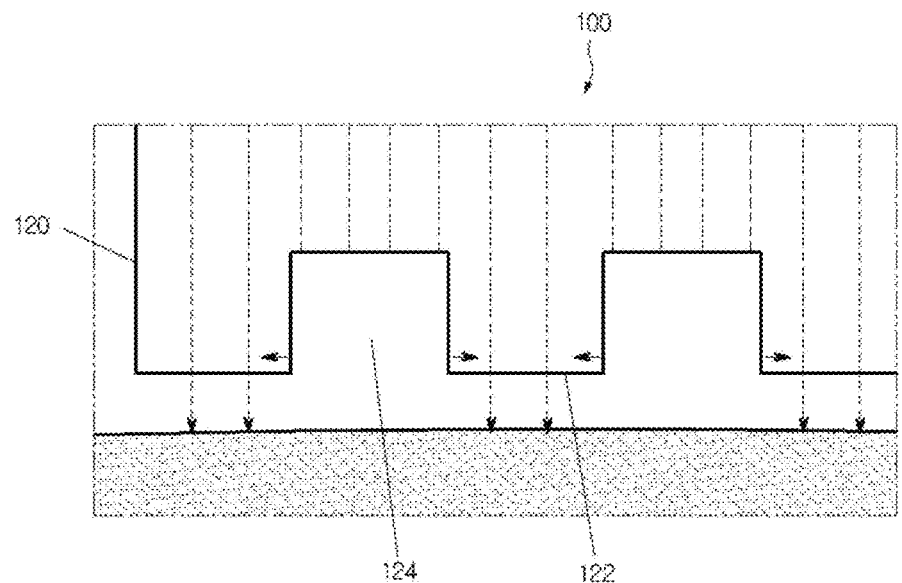
Figure 9:
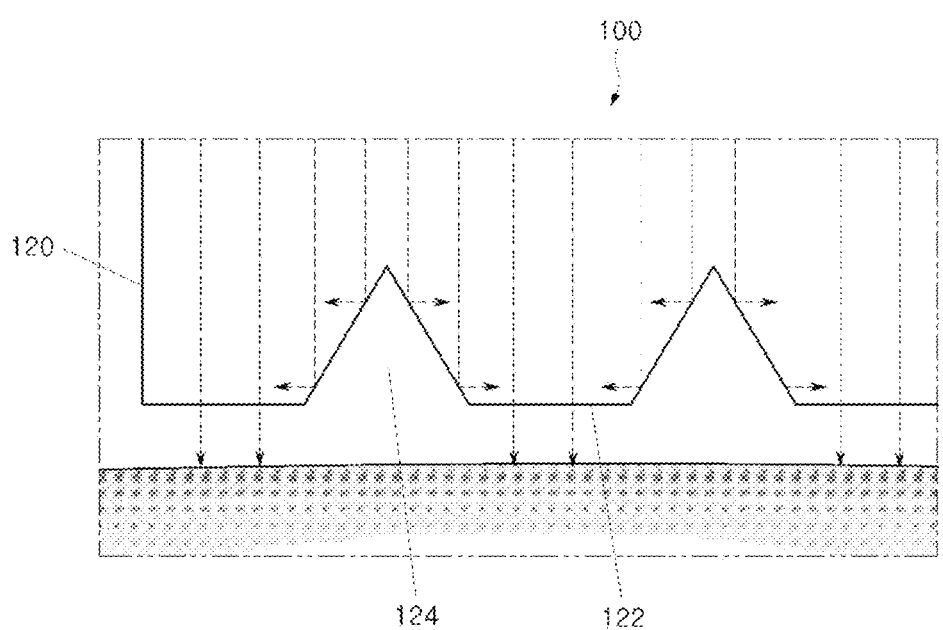
FIG. 9 is an illustrative view showing the state of laser irradiation at the treatment site using lens according to the disclosure.

FIG. 3 shows the relationship between the lens and the light source according to the disclosure. FIG. 4 illustrates the lens according to the disclosure, and FIG. 5 provides a bottom view of the lens. FIGS. 6 through 8 illustrate the shape of the reflecting unit according to the disclosure. FIG. 9 shows the state of the laser irradiation at the treatment site using the lens according to the disclosure.

The lens (100) includes a body (120) with a three-dimensional shape, allowing light emitted from the light source (260) to pass through the body (120) and be irradiated on the bottom surface. Preferably, the body (120) is formed in a cubic shape.

The laser is generated and positioned on the upper surface of the body (120).

According to the disclosure, detailed illustrations of the lens (100) are omitted because the lens can be equipped on the laser irradiator with a handle formed with the laser light source (260) and this well-known configuration can be adapted in various designs.

According to the disclosure, bottom source of the body (120) of the lens (100) includes the concentrating unit (122) and the reflecting unit (124). The concentrating unit (122) are portions where light passing through the body (120) is focused, while the reflecting unit (124) reflect light toward the concentrating unit (122), further concentrating the light at these points.

The concentrating unit (122) and the reflecting unit (124) alternate with each other. This configuration is achieved by forming the concentrating unit (122) at specific intervals with the reflecting unit (124) formed in between.

Pattern of grooves can be formed on the bottom surface of the body (120) to create the reflecting unit (124). Parts of the bottom surface of the body (120) where grooves are not formed naturally become the concentrating unit (122). Therefore, the concentrating unit (122) and the reflecting unit (124) alternate. In this configuration, bottom surface of the body (120) is preferably flat, and the internal walls of the reflecting unit (124) should be sloped.

The reflecting unit (124) are formed by grooves engraved in the bottom surface of the body (120), light passing through the body (120) will be reflected toward the concentrating unit (122) from the boundary surface between the reflecting unit (124) and the body (120). This is due to the prism effect, where some light passes through and some is reflected when it hits the sloped boundary surface, with generally more than 95% of the light being reflected.

The reflecting unit (124) can be formed by engraving grooves in a grid pattern, similar to a woven mesh. As a result, the concentrating unit (122) take on a square protrusion shape, surrounded by the reflecting unit (124) on all four sides, with each side reflecting light toward the concentrating unit (122).

Grooves forming the grid pattern of the reflecting unit (124) can have a triangular cross-section. Accordingly, this naturally forms the boundary surface between the reflecting unit (124) and the body (120) as a sloped surface. The triangle is preferably an isosceles triangle, ensuring that the light reflected from both sides is of equal intensity, allowing for uniform light reflection toward each concentrating unit (122).

Alternatively, grooves forming the grid pattern of the reflecting unit (124) can have a circular cross-section. This results in a convex sloped surface for the boundary surface between the reflecting unit (124) and the body (120), which may result in less reflected light compared to a triangular shape. The intensity of light focused on the concentrating unit (122) or the amount of light passing through the reflecting unit (124) can be adjusted as needed.

Another possible configuration is to form the grooves with a rectangular cross-section.

As a note, while laser light is highly directional due to its focused nature, IPL devices tend to cause light refraction and scattering. This can lead to effects similar to circles or triangles due to the variation in light incidence angles and refraction.

As described above, in IPL light guiding device that realizes fractional by utilizing a polarization function according to the disclosure, light passing through the body (120) is concentrated in the concentrating unit (122) on the bottom surface of the body (120). As a result, during the process of treating the human body with the light irradiator, light is focused on the treatment site, thereby efficiently inducing fractional effects and concentrating energy on the targeted areas for enhanced treatment outcomes.

What is claimed is:

1. An Intense Pulse Light (IPL) light guiding device comprising:
   a handle for manual operation, a light source equipped inside a reflective casing, and an installment section formed below the light source;
   a lens that is detachably coupled to the installment section;
   the lens forming a three-dimensional body allowing light emitted from the light source to pass through and irradiate the bottom surface of the body;
   wherein the bottom surface of the body includes concentrating units irradiated with the light, and reflecting units formed between the concentrating units, which reflect light toward the concentrating units;
   wherein the light emitted from the light source is concentrated and irradiated onto the concentrating units.
2. The IPL light guiding device of claim 1, wherein:
   the bottom surface of the body is flat, the surface comprising grooves forming a specific pattern which form the reflecting units, while the non-grooved portions form the concentrating units;
   wherein the internal walls of the grooves are sloped, reflecting light toward the concentrating units from the boundary surface between the body and the internal area of the reflecting units.
3. The IPL light guiding device of claim 2, wherein:
   the reflecting unit is formed by grooves engraved in a grid pattern.
4. The IPL light guiding device of claim 3, wherein:
   the grooves have a triangular cross section.
5. The IPL light guiding device of claim 4, wherein:
   the triangular cross-section is a isosceles triangle.
6. The IPL light guiding device of claim 3, wherein:
   the grooves have a circular cross section.
7. The IPL light guiding device of claim 3, wherein:
   the grooves have a rectangular cross section.

* * * * *